United States Patent [19]

Whistler

[11] 4,301,276

[45] Nov. 17, 1981

[54] SYNTHESIS OF DAUNOSAMINE HYDROCHLORIDE AND INTERMEDIATES USED IN ITS PREPARATION

[75] Inventor: Roy L. Whistler, West Lafayette, Ind.

[73] Assignee: Purdue University, West Lafayette, Ind.

[21] Appl. No.: 128,299

[22] Filed: Mar. 7, 1980

[51] Int. Cl.³ .............................................. C07H 15/04
[52] U.S. Cl. .................................. 536/4; 260/345.8 R; 536/1; 536/18; 536/53; 424/180
[58] Field of Search ........................... 536/1, 4, 18, 53; 260/345.8 R

[56] References Cited

U.S. PATENT DOCUMENTS

| | | | |
|---|---|---|---|
| 3,953,422 | 4/1976 | Pfeiffer | 536/4 |
| 4,020,270 | 4/1977 | Arcamone et al. | 536/17 A |
| 4,024,333 | 5/1977 | Horton et al. | 536/4 |
| 4,112,076 | 9/1978 | Arcamone et al. | 536/17 A |
| 4,181,795 | 1/1980 | Whistler | 536/17 A |

OTHER PUBLICATIONS

Arcamone, et al., "Carbohydrate Research", 46, C3–C5 1976.
Bargiotti, et al., "Carbohydrate Research", 58, pp. 353–361, 1977.
El Khadem et al., "Carbohydrate Research", 58, pp. 230–234, 1977.
Tanaka, "Carbohydrates", 33, p. 511, #91:5437m, 1979.
Dejter-Juszynski et al., "Carbohydrate Research", 28, pp. 144–146, 1973.
Nayak et al., "Jour. of Organic Chem.", 34, pp. 97–100, 1969.
Blindenbacher et al., "Helvetica. Chimica. Acta." 31, p. 1669, 1948.

*Primary Examiner*—Johnnie R. Brown
*Attorney, Agent, or Firm*—Finnegan, Henderson, Farabow, Garrett & Dunner

[57] ABSTRACT

A process for synthesizing daunosamine hydrochloride is disclosed. Intermediates useful for synthesizing daunosamine hydrochloride, and processes for preparing such intermediates, are also disclosed.

20 Claims, No Drawings

SYNTHESIS OF DAUNOSAMINE HYDROCHLORIDE AND INTERMEDIATES USED IN ITS PREPARATION

FIELD OF INVENTION

The present invention pertains to a technique for synthesizing daunosamine hydrochloride and intermediates which can be converted into daunosamine hydrochloride. The present invention also pertains to certain novel intermediates useful in the synthesis of daunosamine hydrochloride.

BACKGROUND OF THE INVENTION

Doxorubicin is a known anthracycline antibiotic described, e.g., in U.S. Pat. No. 3,590,028. Doxorubicin, and the closely related compound daunomycin, are antineoplastic agents of established clinical utility. Doxorubicin hydrochloride, available from Adria Laboratories, Inc. under the trade name Adriamycin ®, has been approved by the Food and Drug Administration for use in clinical research, and is one of the most powerful anti-cancer drugs available against numerous forms of cancer.

At present, doxorubician is produced commercially from a soil fungus by a fermentation process. A suitable fermentation technique for preparing doxorubicin is described in U.S. Pat. No. 3,590,028. Such techniques are inherently expensive and limit the types of molecules that can be produced. Because of the inherent disadvantages of presently available commercial techniques for producing doxorubicin and such related compounds as daunomycin, substantial effort has been devoted to developing processes for producing such compounds by chemical synthesis.

Doxorubicin consists of an aglycone, adriamycinone, and an amino sugar, daunosamine. Similarly, daunomycin consists of the aglycone daunomycinone, and the amino sugar, daunosamine. Specifically, doxorubician and daunomycin have the formula:

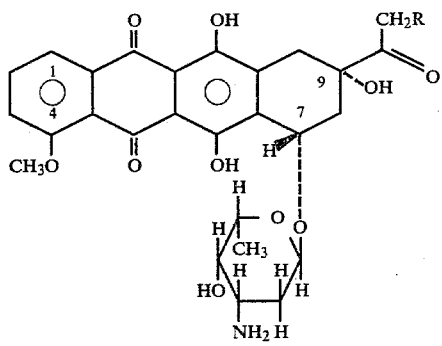

with the compound being doxorubicin when R is —OH and daunomycin when R is —H.

Techniques for synthesizing doxorubicin and daunomycin, and their aglycones, adriamycinone and daunomycinone, are known. See, e.g., Wong et al., Canadian Journal of Chemistry, Vol. 51, p. 466 (1973); Acton et al., Journal of Medicinal Chemistry, Vol, 17, No. 6, p. 659 (1974); Kende et al., Journal of American Chemical Society, Vol. 97, No. 15, p. 4425 (1975) and Vol. 98, No. 7, p. 1967 (1976); and Kende et al, U.S. Pat. No. 4,021,457. Techniques for attaching daunosamine to the aglycones are also known. See, e.g., Acton et al., supra, and Smith et al., Journal of American Chemical Society, Vol. 98, No. 7, p. 1969 (1976).

None of the known techniques for the synthesis of anthracycline antibiotics such as doxorubicin has proven to be commercially successful. Because of the demand for, and scarcity of, these compounds, a commercially practical technique for synthesizing them is greatly needed. Since the sugar daunosamine provides an important part of these compounds, and since it is known both how to synthesize the aglycones adriamycinone and daunomycinone, as well as how to attach daunosamine to the aglycones, techniques for synthesizing daunosamine, and related compounds, are highly desirable as part of a technique for the total synthesis of the anthracycline antibiotics.

While techniques for synthesizing daunosamine are known, the known techniques suffer severe shortcomings that limit their practical utility. For example, the process disclosed in Marsh et al., Chemical Communications, p. 973 (1967) uses a difficult method to obtain glycal as a starting material and involves the use of a potentially hazardous step of making an azide derivative with sodium azide. Furthermore, in the process disclosed by Marsh et al., isomers are produced that require separation by a difficult chromatographic step. The process disclosed in Horton et al., Carbohydrate Research, Vol. 44, p. 227 (1975), requires the use of a number of very expensive reagents and also results in the production of difficult to separate isomers.

In U.S. Patent Application Ser. No. 908,240, filed May 22, 1978, and which issued as U.S. Pat. No. 4,181,795, a process for synthesizing daunosamine and related compounds, as well as novel intermediates, is disclosed. In U.S. Patent Application Ser. No. 128,298, filed concurrently herewith, disclosed is, inter alia, a process for synthesizing alkyl L-ristosaminides and N-benzoyl-L-ristosamine, ristosamine being a configurational analog of daunosamine.

The present invention provides a practical technique for synthesizing daunosamine hydrochloride. In addition, the present invention provides novel intermediates, and methods for their preparation, valuable in synthesizing daunosamine hydrochloride. Moreover, the synthesis techniques disclosed herein may use, as starting materials, the readily available and inexpensive compounds D-glucose and D-galactose.

SUMMARY OF THE INVENTION

In accordance with the present invention, the known compounds L-fucal or 6-deoxy-L-idal, which compounds may be derived from D-galactose and D-glucose, respectively, are used as starting materials to produce alkyl L-daunosaminides. These latter compound may be converted to L-daunosamine hydrochloride.

The process of the present invention for synthesizing alkyl L-daunosaminides involves:

a. oxidizing either L-fucal or 6-deoxy-L-idal;

b. reacting the resultant 1,5-anhydro-3-oxo-2,3,6-trideoxy-L-threo-hex-1-enitol with a blocking agent to produce a compound having the formula

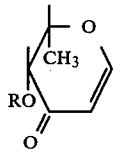

wherein R is a blocking group;

c. subjecting the resultant compound to alkyloxymercuration to produce a ketose having the formula

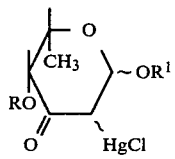

wherein $R^1$ is $C_1$–$C_6$ alkyl;

d. subjecting the resultant ketose to oximation to produce an oxime having the formula

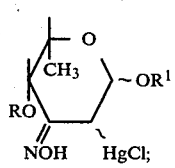

e. demercurating the oxime to a compound having the formula

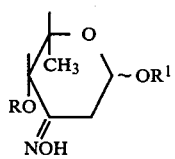

and;

f. reducing the resultant compound with simultaneous removal of the blocking group to produce alkyl L-daunosaminides.

The L-fucal used in step (a) may be prepared by acetylating L-fucose; brominating the resultant fucose tetraacetate to produce 2,3,4-tri-O-acetyl-L-fucopyranosyl bromide; reducing said bromide to produce 3,4-di-O-acetyl-L-fucal; and deacetylating said fucal to produce L-fucal.

The 6-deoxy-L-idal used in step (a) may be prepared by acetylating 6-deoxy-L-idose; brominating the resultant idose tetraacetate to produce 2,3,4-tri-O-acetyl-6-deoxy-L-idopyranosyl bromide; reducing said bromide to produce 3,4-di-O-acetyl-6-deoxy-L-idal; and deacetylating said idal to produce 6-deoxy-L-idal.

While the compound produced by step (e) can be directly reduced with simultaneous removal of the blocking group, it is preferable to first react it with a blocking agent to produce a compound having the formula:

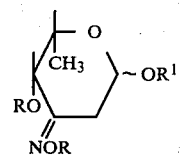

wherein R is a blocking group, and then reducing the resultant compound with simultaneous removal of the blocking groups to produce alkyl L-daunosaminides.

The alkyl L-daunosaminides produced by the above-described process may be converted to L-daunosamine hydrochloride by reacting the daunosaminide with hydrochloric acid.

The present invention also pertains to novel intermediates, and methods for their preparation, useful in synthesizing daunosamine hydrochloride. Among such intermediates are those having the formula:

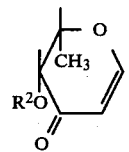

wherein $R^2$ is

or H.

The present invention additionally provides valuable intermediates, and methods for their preparation, useful in synthesizing daunosamine hydrochloride including those having the formula:

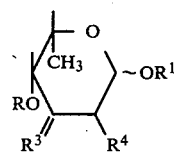

wherein
$R^1$ is $C_1$–$C_6$ alkyl
R is

$R^3$ is O=, HON=,

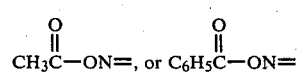

$R^4$ is HgCl or H
provided that when $R^4$ is HgCl, $R^3$ must be O= or HON=; when $R^4$ is H, $R^3$ cannot be O=.

DESCRIPTION OF PREFERRED EMBODIMENTS

In the synthesis technique of the present invention D-galactose, a readily available and inexpensive compound, may be used as a starting material. Using the method described in Dejter-Juszynski and Flowers, *Synthesis of L-fucose,* Carbohydrate Research, Vol. 28, pp. 144-146 (1973), D-galactose is converted into L-fucose having the formula:

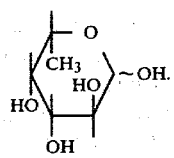

1

Parenthetically, in the above structural formula, as well as in other structural formulas appearing herein, some of the hydrogen atoms are omitted for the sake of clarity. Those skilled in the art will have no trouble comprehending the formulas to include the omitted hydrogen atoms.

L-Fucose is then acetylated with acetic anhydride to produce fucose tetraacetate. Preferably, the reaction is carried out by suspending the L-fucose in a solvent, such as pyridine, and slowly adding the acetic anhydride. The mixture is stirred, poured into a separating funnel containing ice water, and extracted with chloroform. The organic extracts are washed with water, aqueous sodium bicarbonate, and dried over magnesium sulfate. The mixture is filtered and the solvent removed under reduced pressure. The residue is co-evaporated with toluene to remove any remaining pyridine or acetic acid. The fucose tetraacetate is then brominated to produce 2,3,4-tri-O-acetyl-L-fucopyranosyl bromide having the formula:

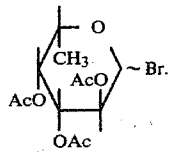

2

It is to be noted that in the above formula, and elsewhere herein, the use of "Ac" is understood to represent the acetyl radical, i.e.,

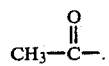

The fucose tetraacetate is brominated with hydrogen bromide in acetic acid. The mixture is worked up similarly to that just described for preparing fucose tetraacetate, i.e., chloroform extraction from ice water.

The bromide of formula 2 is then reduced to produce 3,4-di-O-acetyl-L-fucal having the formula:

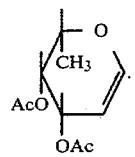

3

Reduction is carried out by treating a mixture of the bromide of formula 2, and a solution of acetic acid containing sodium acetate, with activated zinc dust. The reaction mixture is then filtered and extracted with chloroform. The organic layer is then washed with aqueous sodium bicarbonate and water, dried over magnesium sulfate, filtered, and the solvent removed under reduced pressure. The formula 3 compound is then purified by vacuum distillation to a syrup which crystallizes on standing.

The compound of formula 3 is deacetylated to produce L-fucal having the formula:

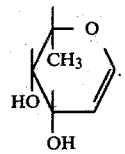

4

Deacetylation is effected by dissolving the formula 3 compound in methanol, and adjusting the pH to 8 to 9 by the addition of sodium methoxide in methanol. The reaction mixture is then neutralized and the solvent is removed by evaporation. The crude L-fucal is then purified by recrystallization.

As an alternative to the above-described procedure which uses D-galactose as a starting material, D-glucose may be used as a starting material.

D-Glucose is first converted to 5,6-anhydro-3-O-benzyl-1,2-O-isopropylidene-β-L-idofuranose by the procedure described in Nayak and Whistler, *Improved Syntheses of 5-Thio-D-glucose,* J. Organic Chem., Vol. 34, p. 97 (1969). The latter compound is converted to 6-deoxy-1,2-O-isopropylidene-β-L-idofuranose according to the procedure described in Blidenbacker and Reichstein, *Synthese des L-Glucomethylose-3-methylathers und seine Identifizierung mit Thevetose,* Helvetica Chimica Acta, Vol. 31, p. 1669 (1948). Hydrolysis of this compound will give 6-deoxy-L-idose having the formula:

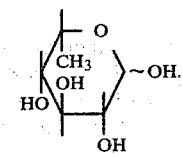

1'

Hydrolysis is carried out in 0.05M H₂SO₄ at 50° C. for 16 hours under nitrogen.

This compound is converted to 2,3,4-tri-O-acetyl-6-deoxy-L-idopyranosyl bromide having the formula:

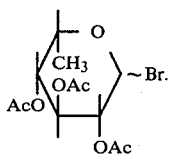

2'

The procedure for conducting the conversion is identical to that described for converting L-fucose (compound 1) to the compound of formula 2, the previous procedure being followed exactly with 6-deoxy-L-idose being substituted for L-fucose.

The compound of formula 2' is reduced to 3,4-di-O-acetyl-6-deoxy-L-idal having the formula:

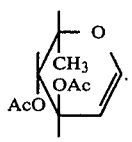

3'

The procedure for reducing the formula 2' compound to the formula 3' compound is identical to that described for reducing the formula 2 compound to the formula 3 compound, the formula 2' compound merely being substituted for the formula 2 compound. The formula 3' compound is purified by distillation and/or recrystallization.

The compound of formula 3' is then deacetylated to 6-deoxy-L-idal having the formula:

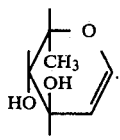

4'

The procedure for carrying out the deacetylation is identical to that described for deacetylating the formula 3 compound to the formula 4 compound, the formula 3' compound merely being substituted for the formula 3 compound.

The next step in the synthesis of alkyl L-daunosaminides is to oxidize the compound of either formula 4 or 4' to produce 1,5-anhydro-3-oxo-2,3,6-trideoxy-L-threo-hex-1-enitol having the formula:

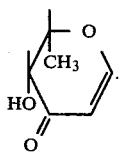

5

Oxidation is preferably conducted by dissolving in a flask either the compound of formula 4 or 4' in benzene, and then adding silver carbonate on celite (Fetizon's reagent). The mixture is distilled to remove part of the solvent, and then refluxed. The mixture is then filtered through celite and the filtrate evaporated under reduced pressure to give the compound of formula 5.

The Fetizon's reagent used in the above oxidation step is prepared by dissolving silver nitrate in distilled water, adding celite, and then adding a solution of potassium bicarbonate in distilled water. The well-stirred suspension is filtered to collect the reagent, which reagent is then dried. The Fetizon's reagent is stored in a brown glass bottle at room temperature.

An an alternative preferable oxidation step, either the compound of formula 4 or 4' can be reacted with a specially prepared suspension of manganese dioxide in tetrahydrofuran. The manganese dioxide used in this step is prepared by dissolving potassium permanganate in distilled water, heating, and adding simultaneously manganese sulfate monohydrate in water and a solution of sodium hydroxide. The suspension is stirred, filtered, and washed. The resultant chocolate-brown solid is then dried to produce a manganese dioxide satisfactory for use in the oxidation step.

As a further alternative preferable oxidation step, either the compound of formula 4 or 4' can be reacted with chromium trioxide:pyridine complex in methylene chloride catalyzed by acetic anhydride.

The compound of formula 5 is then reacted with a blocking agent to produce a compound having the formula:

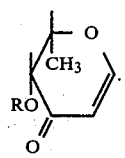

6 wherein R is a blocking group.

Examples of suitable blocking groups which may be used throughout the present synthesis technique include acetyl

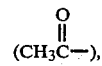

and benzoyl

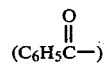

groups. These groups may be introduced by reacting the compound of formula 5 with, respectively, such compounds as acetic anhydride or benzoyl chloride. The reaction is preferably conducted in a solvent which is a good acid receptor, such as pyridine, sodium hydroxide solution, or quinoline. Subsequent to the reaction, the solvent is removed under reduced pressure, and the residue is co-evaporated several times with toluene. The product is purified by distillation, recrystallization, and/or column chromatography. When the preferred reactant, acetic anhydride, is reacted with the compound of formula 5, 1,5-anhydro-3-oxo-4-O-acetyl-2,3,6-trideoxy-L-threo-hex-1-enitol is produced.

The compound of formula 6 is next subjected to alkyloxymercuration to produce a ketose having the formula:

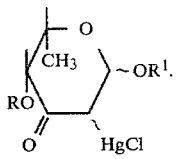

wherein R is a blocking group as previously described, and $R^1$ is $C_1$-$C_6$ alkyl. When R is the preferred acetyl group and $R^1$ is methyl, this compound would be methyl 2-chloromercuri-3-oxo-4-O-acetyl-2,3,6-trideoxy-L-(xylo, lyxo)-hexopyranoside. Alkyloxymercuration is preferably conducted by dissolving mercuric acetate and mercuric chloride in methanol, and refluxing the mixture. The compound of formula 6, as a solution in methanol, is then added to the refluxed mixture. When the reaction is complete, the solvent is removed and the residue is co-evaporated several times with toluene to remove the acetic acid formed in the reaction. The product is purified by recrystallization or column chromatography.

The ketose of formula 7 is then subjected to oximation to produce an oxime having the formula:

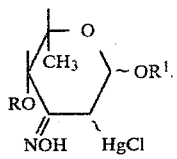

wherein R and $R^1$ are as previously described. When R is the preferred acetyl group and $R^1$ is methyl, this compound would be methyl 2-chloromercuri-3-oximino-4-O-acetyl-2,3,6-trideoxy-L-(xylo, lxyo)-hexopyranoside. Oximation can be effected by reacting the ketose of formula 7 with hydroxylamine.

The compound of formula 8 is next subjected to demercuration to produce a compound having the formula:

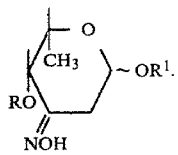

wherein R and $R^1$ are as previously described. When R is the preferred acetyl group and $R^1$ is methyl, the compound would be methyl 3-oximino-4-O-acetyl-2,3,6-trideoxy-L-threo-hexopyranoside. Preferably, demercuration is effected by dissolving the formula 8 compound in methanol, and adding triethylamine followed by sodium borohydride. The resulting suspension is filtered through celite to remove elemental mercury, and the filtrate is evaporated. The residue is slurried in hot diethyl ether and filtered to remove triethylammonium chloride. The filtrate is evaporated to provide the compound of formula 9, which compound can be purified by recrystallization or column chromatography.

While the oxime of formula 9 could be directly reduced with simultaneous removal of the blocking group to produce alkyl L-daunosaminides, it is preferable to first react it with a blocking agent to produce a compound having the formula:

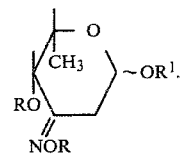

wherein R and $R^1$ are as previously described. The blocking agent can be the same as those compounds reacted with the compound of formula 5, namely, acetic anhydride or benzoyl chloride. As with the previously described reaction involving the formula 5 compound, the reaction involving the oxime of formula 9 is preferably conducted in a solvent which is a good acid receptor, such as pyridine, sodium hydroxide solution, or quinoline. When the preferred reactant, acetic anhydride, is reacted with the preferred oxime of formula 9 and when $R^1$ is methyl, methyl 3-acetyloximino-4-O-acetyl-2,3,6-trideoxy-L-threo-hexopyranoside is produced.

The compound of formula 10 is next reduced with simultaneous removal of the blocking groups to produce alkyl L-daunosaminides having the formula:

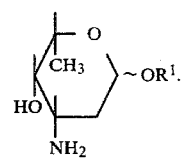

When $R^1$ is methyl, this compound is methyl L-daunosaminide. The reduction is preferably effected by dissolving the formula 10 compound in tetrahydrofuran, and then adding, as the reducing agent, lithium aluminum hydride, followed by refluxing. Water, followed by sodium hydroxide, is then added. The mixture is then filtered through celite, and the solvent is removed. The daunosaminide of formula 11 can then be purified by recrystallization or column chromatography.

The compound of formula 11 may, if desired, be converted to L-daunosamine hydrochloride having the formula:

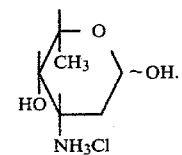

The conversion can be effected by dissolving the formula 11 compound in hydrochloric acid. The solution is decolorized with charcoal, filtered through celite, and evaporated. The resulting material crystallizes on addition of acetone.

L-Daunosamine hydrochloride can be converted to a derivative suitable for reaction with the aglycones adriamycinone, as the 14-p-methoxytrityl derivative, or daunomycinone, using techniques known in the art. For example, according to the method of Acton et al, supra, L-daunosamine hydrochloride is allowed to react with trifluoracetic anhydride to give N-trifluoroacetyl-L-daunosamine, which is treated with p-nitrobenzoyl chloride giving, in turn, 1,4-bis-(O-p-nitrobenzoyl)-N-trifluoroacetyl-L-daunosamine. Treatment of this substance with anhydrous hydrogen bromide produces 4-(O-p-nitrobenzoyl)-N-trifluoroacetyl-L-daunosaminyl bromide. The sugar bromide can be condensed with daunomycinone or the blocked adriamycinone derivative in the presence of mercuric cyanide, mercuric bromide, and powdered molecular sieve to produce daunorubicin hydrochloride or doxorubicin hydrochloride depending on the aglycone used, after removal of the blocking groups.

The following examples further illustrate preferred embodiments of the present invention. The examples should in no way be considered limiting, but are merely illustrative of the various features of the present invention.

EXAMPLE 1

To a suspension of 10 grams of L-fucose in 50 milliliters of pyridine is slowly added 50 milliliters of acetic anhydride. The mixture is stirred for 1 to 2 days at room temperature and then poured into a separatory funnel containing ice water. The resulting mixture is extracted 3 to 4 times with 50 milliliter portions of chloroform. The organic extracts are washed with water, aqueous sodium bicarbonate, and dried over magnesium sulfate. The mixture is filtered and the solvent removed under reduced pressure to give a residue of crude fucose tetraacetate. The crude tetraacetate is co-evaporated several times with toluene to remove any remaining pyridine or acetic acid. The fucose tetraacetate is then treated with 32% hydrogen bromide and acetic acid for 2 hours, and the mixture is then worked up similarly to that just described for the tetraacetate, i.e., chloroform extraction from an ice water mixture. The resultant crude product is 2,3,4-tri-O-acetyl-L-fucopyranosyl bromide.

EXAMPLE 2

The previous procedure for producing the fucopyranosyl bromide is followed exactly, except that 6-deoxy-L-idose is substituted for L-fucose. The product is 2,3,4-tri-O-acetyl-6-deoxy-L-idopyranosyl bromide.

EXAMPLE 3

The crude product of Example 1, in a 50% solution of acetic acid containing sodium acetate, is treated with activated zinc dust. The temperature of the reaction was maintained at 0° to 10° C. for 2 to 3 hours. The reaction mixture was then filtered and extracted with chloroform. The organic layer was washed with aqueous sodium bicarbonate and water, dried over magnesium sulfate, filtered, and the solvent removed under reduced pressure. The resultant 3,4-di-O-acetyl-L-fucal is purified by vacuum distillation to give a syrup which crystallizes on standing and has a melting point of 47°–49° C.

EXAMPLE 4

The identical procedure just described in Example 3 is followed, except that the crude product of Example 2 is substituted for the crude product of Example 1. The resultant 3,4-di-O-acetyl-6-deoxy-L-idal is purified by distillation and/or recrystallization.

EXAMPLE 5

10 grams of the product of Example 3 is dissolved in 100 milliliters of methanol, and the pH is adjusted by 8–9 by the dropwise addition of a solution of sodium methoxide in methanol. The mixture is allowed to stand overnight at 0°–5° C. after which time deacetylation has taken place as judged by thin-layer chromatography (t.l.c.) monitoring. The reaction mixture is neutralized with a few drops of acetic acid and the solvent is removed by evaporation. The crude L-fucal is purified by recrystallization from appropriate solvents.

EXAMPLE 6

The identical procedure just described in Example 5 is followed, except that the product of Example 4 is substituted for the product of Example 3. The resultant product is 6-deoxy-L-idal.

EXAMPLE 7

In a 250 milliliter round-bottomed flask, 1 gram of L-fucal [Example 5 product] is dissolved in 100 milliliters of benzene. To this solution was added 20–25 grams of silver carbonate on celite (Fetizon's reagent), prepared as described below, and the mixture was stirred. The flask was equipped for simple distillation, and 20–25 milliliters of solvent was removed by distillation. During this time the yellow Fetizon's reagent becomes dark brown. The distillation assembly is replaced with an efficient reflux condenser and the mixture is refluxed for 1 hour, after which time the reaction is generally completed as judged by t.l.c. monitoring. The hot mixture is filtered through celite and the filtrate evaporated under reduced pressure to give 1,5-anhydro-3-oxo-2,3,6-trideoxy-L-threo-hex-1-enitol.

Preparation of Fetizon's Reagent

In 200 milliliters of distilled water is dissolved 34 grams of silver nitrate, followed by 30 grams of celite. Then, cautiously and in several portions, is added a solution of 21 grams of potassium bicarbonate in 300 milliliters of distilled water. Ten minutes after the final addition of the bicarbonate solution, the well stirred suspension is filtered to collect the reagent. The reagent is air-dried for 15–30 minutes and then transferred to a 1 liter flask and put on a rotary evaporator for several hours to remove most of the water. The yield of Fetizon's reagent was 58 grams. The reagent is stored in a brown glass bottle to protect it from light and left at room temperature.

EXAMPLE 8

As an alternative to the procedure of Example 7, 1 gram of L-fucal may be oxidized by 15–20 grams of specially prepared manganese dioxide (described below) in tetrahydrofuran at room temperature. As with the procedures of Example 7, the product is 1,5-anhydro-3-oxo-2,3,6-trideoxy-L-threo-hex-1-enitol. The disadvantage to this procedure is the extended reaction time of 24 to 48 hours. However, the oxidant is relatively inexpensive and easy to prepare.

Preparation of Activated Manganese Dioxide

48 Grams of potassium permanganate in 300 milliliters of distilled water was heated to 90° C. To this solution was added simultaneously 42 grams of manganese sulfate monohydrate in 75 milliliters of water and 60 milliliters of 40% sodium hydroxide over a period of 15–20 minutes. The suspension was stirred at 85°–90° C. for 1 hour, filtered, and washed with water until the washings are clear. The chocolate-brown solid is dried overnight at 160° C. to yield 41 grams of manganese dioxide.

EXAMPLE 9

As a second alternative to the procedure of Example 7, 4 grams of chromium trioxide is added to a solution of methylene chloride containing 1.61 milliliters of pyridine and the mixture is stirred at 25° C. for 15 minutes. To this solution is added 1.3 grams of L-fucal immediately followed by the addition of 0.95 milliliters of acetic anhydride, the reaction being monitored by t.l.c. The reaction is generally complete in 5–10 minutes. The reaction mixture is then poured onto a silica gel column which has an amount of ethyl acetate above it to precipitate the chromium compounds, and the product is eluted as one fraction. The resulting 1,5-anhydro-3-oxo-2,3,6-trideoxy-L-threo-hex-1-enitol is purified by recrystallization.

EXAMPLE 10

The procedure identical to that described in Example 7 is followed, except that 6-deoxy-L-idal [Example 6 product] is substituted for L-fucal. The same product is formed.

EXAMPLE 11

The procedure identical to that described in Example 8 is followed, except that 6-deoxy-L-idal is substituted for L-fucal. The same product is formed.

EXAMPLE 12

The procedure identical to that described in Example 9 is followed, except that 6-deoxy-L-idal is substituted for L-fucal. The same product is formed.

EXAMPLE 13

The compound produced in Examples 7–12 (1,5-anhydro-3-oxo-2,3,6-trideoxy-L-threo-hex-1-enitol) is treated with acetic anhydride:pyridine (1:1) overnight at room temperature. The solvent is then removed under reduced pressure and the residue is co-evaporated several times with toluene to insure complete removal of acetic anhydride and pyridine. The resulting crude 1,5-anhydro-3-oxo-4-O-acetyl-2,3,6-trideoxy-L-threo-hex-1-enitol is purified by distillation, recrystallization, and/or column chromatography.

EXAMPLE 14

Freshly recrystallized mercuric acetate (0.5 mole equivalent) and crystalline mercuric chloride (0.5 mole equivalent) are dissolved/suspended in reagent methanol (70 milliliters methanol/gram Hg (II) salt) and the mixture is brought to reflux. After 1–1.5 hours the solution is cooled to room temperature and the compound produced by Example 13 (1 mole equivalent) is added as a solution in methanol. The mixture is stirred for several hours at room temperature and the reaction is monitored via t.l.c. for the presence of the slower moving 2-chloromercuri derivatives. When the reaction is complete as judged by t.l.c. monitoring the solvent is removed under reduced pressure and the residue co-evaporated several times with toluene to remove the acetic acid formed in the reaction. The crude resulting methyl 2-chloromercuri-3-oxo-4-O-acetyl-2,3,6-trideoxy-L-(xylo,lyxo)-hexapyranoside is purified by recrystallization or column chromatography.

EXAMPLE 15

Freshly recrystallized hydroxylamine hydrochloride (6 mole equivalents) and potassium hydroxide (6 mole equivalents) are dissolved in 99.5% ethanol (100 milliliters of ethanol/gram $NH_2OH$ HCl) and the resulting potassium chloride filtered. The compound produced by Example 14 (1 mole equivalent) is then dissolved in ethanol and added to the solution of excess hydroxylamine. The white cloudy mixture is stirred overnight at room temperature. The resulting powdery methyl 2-chloromercuri-3-oximino-4-O-acetyl-2,3,6-trideoxy-L-(xylo,lyxo)-hexapyranoside is filtered and more may be recovered by suitable processing of the filtrate. Purification by recrystallization follows.

EXAMPLE 16

The product of Example 15 (1 mole equivalent) is dissolved in reagent methanol (25 milliliters methanol/gram of product of Example 15) and the solution is cooled to 0° C. Triethylamine (3.5 mole equivalents) is quickly added to this solution, quickly followed by the addition, in several portions, of sodium borohydride (0.5 mole equivalents). Immediate demercuration is noted. The suspension is stirred for 10 minutes at 0° C. and then for 20–30 minutes at room temperature. The elemental mercury is removed by filtration through a layer of celite and the filtrate is evaporated under reduced pressure. The residue is slurried in hot diethyl ether and filtered to remove the insoluble triethylammonium chloride. The ethereal filtrate is evaporated to provide crude methyl 3-oximino-4-O-acetyl-2,3,6-trideoxy-L-threo-hexapyranoside which may be purified by recrystallization or column chromatography.

EXAMPLE 17

The compound produced in Example 16 is dissolved in an excess of acetic anhydride:pyridine (1:1) and stirred overnight at room temperature. The solvent is evaporated under reduced pressure and the residue is co-evaporated with toluene several times to remove the last traces of pyridine and/or acetic anhydride. The resulting methyl 3-acetyloximino-4-O-acetyl-2,3,6-trideoxy-L-threo-hexapyranoside is purified by recrystallization.

EXAMPLE 18

The compound produced in Example 17 (1 mole equivalent) is dissolved in tetrahydrofuran at 0° C., and the solution is de-gassed by bubbling dry nitrogen through it for 10–15 minutes. Portions of lithium aluminum hydride (2 mole equivalents) are slowly added with vigorous stirring. The reaction is allowed to proceed at 0° C. for 30 minutes and then the mixture is refluxed under nitrogen for 1–2 hours. Completion of the reduction may be judged by t.l.c. monitoring (a strong, slow-moving ninhydrin positive spot is observed). Water is cautiously added followed by 1 N sodium hydroxide to destroy the excess hydride. The mixture is filtered through celite and the solvent is removed under reduced pressure. The resulting methyl L-daunosaminide is purified by recrystallization or column chromatography.

EXAMPLE 19

The compound produced in Example 18 is dissolved in 0.5 N hydrochloric acid and is heated for 3 hours at 100° C. The solution is decolorized with charcoal, filtered through celite, and evaporated under reduced pressure. The resulting L-daunosamine hydrochloride crystallizes on addition of acetone, and has a melting point of 168° C.–170° C.

What is claimed is:

1. A process for making alkyl L-daunosaminides comprising:
 a. oxidizing either L-fucal or 6-deoxy-L-idal;
 b. reacting the resultant 1,5-anhydro-3-oxo-2,3,6-trideoxy-L-threo-hex-1-enitol with a blocking agent to produce a compound having the formula

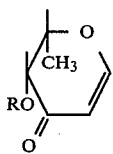

wherein R is a blocking group;
 c. subjecting the resultant compound to alkyloxymercuration to produce a ketose having the formula

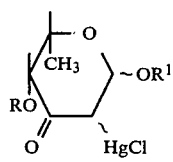

wherein $R^1$ is $C_1$–$C_6$ alkyl;
 d. subjecting the resultant ketose to oximation to produce an oxime having the formula

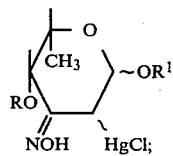

e. demercurating the oxime to a compound having the formula

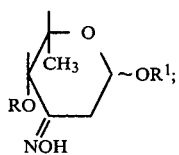

and
 f. reducing the resultant compound with simultaneous removal of the blocking group to produce alkyl L-daunosaminides.

2. The process of claim 1 wherein step (f) comprises reacting the compound produced by step (e) with a blocking agent to produce a compound having the formula

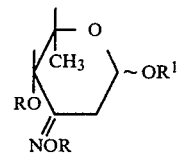

wherein R is a blocking group, and then reducing the resultant compound with simultaneous removal of the blocking groups to produce alkyl L-daunosaminides.

3. The process of claim 2 wherein L-fucal is prepared by a method comprising acetylating L-fucose; brominating the resultant fucose tetraacetate to produce 2,3,4-tri-O-acetyl-L-fucopyranosyl bromide; reducing said bromide to produce 3,4-di-O-acetyl-L-fucal; and deacetylating said fucal to produce L-fucal.

4. The process of claim 2 wherein 6-deoxy-L-idal is prepared by a method comprising acetylating 6-deoxy-L-idose; brominating the resultant idose tetraacetate to produce 2,3,4-tri-O-acetyl-6-deoxy-L-idopyranosyl bromide; reducing said bromide to produce 3,4-di-O-acetyl-6-deoxy-L-idal; and deacetylating said idal to produce 6-deoxy-L-idal.

5. The process of claim 2 wherein alkyl L-daunosaminides are converted to L-daunosamine hydrochloride by reacting said daunosaminide with hydrochloric acid.

6. A process for producing 1,5-anhydro-3-oxo-2,3,6-trideoxy-L-threo-hex-1-enitol comprising oxidizing L-fucal or 6-deoxy-L-idal.

7. A process for producing 1,5-anhydro-3-oxo-4-O-acetyl-2,3,6-trideoxy-L-threo-hex-1-enitol comprising acetylating 1,5-anhydro-3-oxo-2,3,6-trideoxy-L-threo-hex-1-enitol.

8. A process for producing methyl 2-chloromercuri-3-oxo-4-O-acetyl-2,3,6-trideoxy-L-(xylo,lyxo)-hexopyranoside comprising subjecting 1,5-anhydro-3-oxo-4-O-acetyl-2,3,6-trideoxy-L-threo-hex-1-enitol to methoxymercuration.

9. A process for producing methyl 2-chloromercuri-3-oximino-4-O-acetyl-2,3,6-trideoxy-L-(xylo,lyxo)-hexopyranoside comprising subjecting methyl 2-chloromercuri-3-oxo-4-O-acetyl-2,3,6-trideoxy-L-(xylo,lyxo)-hexopyranoside to oximation.

10. A process for producing methyl 3-oximino-4-O-acetyl-2,3,6-trideoxy-L-threo-hexopyranoside comprising demercurating methyl 2-chloromercuri-3-oximino-4-O-acetyl-2,3,6-trideoxy-L-(xylo,lyxo)-hexopyranoside.

11. A process for producing methyl 3-acetyloximino-4-O-acetyl-2,3,6-trideoxy-L-threo-hexopyranoside comprising acetylating methyl 3-oximino-4-O-acetyl-2,3,6-trideoxy-L-threo-hexopyranoside.

12. A process for producing methyl L-daunosaminide comprising reducing methyl 3-acetyloximino-4-O-acetyl-2,3,6-trideoxy-L-threo-hexopyranoside with simultaneous deacetylation.

13. A compound having the formula

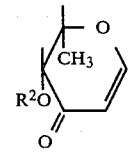

wherein $R^2$ is

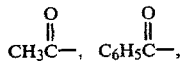

or H.

14. The compound of claim 13 wherein $R^2$ is H.
15. The compound of claim 13 wherein $R^2$ is

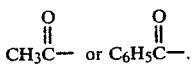

16. A compound having the formula

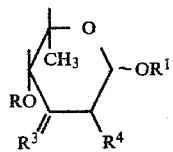

wherein
$R^1$ is $C_1$–$C_6$ alkyl
R is

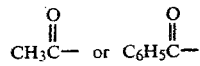

$R^3$ is O=, HON=,

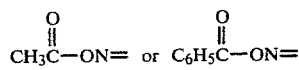

$R^4$ is HgCl or H
provided that when $R^4$ is HgCl, $R^3$ must be O= or HON=; when $R^4$ is H, $R^3$ cannot be O=.

17. The compound of claim 16 wherein $R^3$ is O= and $R^4$ is HgCl.
18. The compound of claim 16 wherein $R^3$ is HON= and $R^4$ is HgCl.
19. The compound of claim 16 wherein $R^3$ is HON= and $R^4$ is H.
20. The compound of claim 16 wherein $R^3$ is

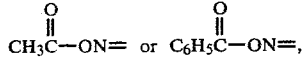

and $R^4$ is H.

* * * * *